United States Patent [19]

Goossens et al.

[11] 4,182,787
[45] Jan. 8, 1980

[54] OPTICALLY TRANSPARENT, RADIOGRAPHICALLY OPAQUE TUBING

[75] Inventors: John C. Goossens, Mt. Vernon, Ind.; Richard E. Molari, Jr., Pittsfield, Mass.

[73] Assignee: General Electric Company, Pittsfield, Mass.

[21] Appl. No.: 917,062

[22] Filed: Jun. 19, 1978

[51] Int. Cl.$^2$ .................. A61M 25/00; F16L 11/04; F16L 11/12

[52] U.S. Cl. .................. 428/36; 128/348; 128/349 R; 138/118; 138/377; 250/519; 252/478; 528/29

[58] Field of Search .......... 428/36; 128/348, 349 R, 128/349 B, 349 BV, 350 R, 350 V, 351, 2 M; 138/118, 177

[56] References Cited

U.S. PATENT DOCUMENTS

| | | | |
|---|---|---|---|
| 3,189,662 | 6/1965 | Vaughn, Jr. | 260/824 |
| 3,336,918 | 8/1967 | Jeckel | 128/348 |
| 3,529,633 | 9/1970 | Vaillancourt | 138/177 |
| 3,608,555 | 9/1971 | Greyson | 128/348 |
| 3,645,955 | 2/1972 | Flynn | 128/348 |
| 3,749,134 | 7/1973 | Slingluff | 128/348 |
| 3,821,325 | 6/1974 | Merritt, Jr. | 260/824 |
| 3,832,419 | 8/1974 | Merritt, Jr. | 260/824 |
| 4,027,659 | 6/1977 | Slingluff | 428/36 |

Primary Examiner—Ellis P. Robinson
Attorney, Agent, or Firm—Myron B. Kapustij; William F. Mufatti

[57] ABSTRACT

Flexible, biologically compatible, optically non-opaque and x-ray opaque tubing for use as a catheter comprised of an organopolysiloxane-polycarbonate terpolymer.

15 Claims, No Drawings

OPTICALLY TRANSPARENT, RADIOGRAPHICALLY OPAQUE TUBING

The instant invention relates to a flexible tubing for use as a catheter which is radiographically opaque, optically non-opaque, preferably optically transparent, and biologically inert, i.e., can be tolerated by body tissues and does not break down upon exposure to body tissues and fluids. The tubing is comprised of a polycarbonate-organopolysiloxane terpolymer having carbonate, halogenated carbonate, and polydiorganosiloxane constituents.

BACKGROUND OF THE INVENTION

In certain types of medical procedures which involve the insertion of catheters into the body, it is often necessary that the location of the catheter be precisely known. The location of the catheter is usually accomplished by means of radiographic observation. In order to employ radiographic means to determine the position of the catheter in the body, such as in a body cavity or in a vein or artery, the catheter must be at least partially opaque to x-rays. However, optimally, the catheter must not only be at least partially opaque to x-rays, but should also be flexible, strong, transparent to visible light, non-toxic, biologically compatible, stable upon contact with biological fluids, tissues, or drugs which are to be administered intravenously or otherwise, and should be able to withstand cleaning and sterilization procedures.

In the prior art, a number of different approaches have been used to render catheters opaque to x-rays. These have included applying a radiographically opaque substance onto the outer surface of the catheter and incorporating an x-ray opaque material within the catheter to thereby render the entire catheter radiographically opaque, as for example in U.S. Pat. No. 3,749,134. The approach of applying x-ray opaque markings to the outer surface of the catheter includes an extra step in the production of the catheter, which adds to the expense of the production of the catheter and to the catheter itself. Furthermore, these external markings are after destroyed or rendered relatively ineffective through cleaning or sterilization of the catheter. The approach of incorporating a radiographically opaque material into the catheter suffers from the drawback that these materials oftentimes render the catheter not only radiographically opaque, but also opaque to visible light. In the cases wherein these materials do not render the catheter optically opaque, there is present the disadvantage of having to incorporate an additional additive to the catheter material.

The present invention provides tubing which overcomes these disadvantages of the prior art and which meets all of the criteria necessary for a successful catheter for use in the medical and biological fields.

DESCRIPTION OF THE INVENTION

The tubing of the instant invention is comprised of a terpolymer of polycarbonate-polydiorganosiloxane having carbonate, halocarbonate and polydiorganosiloxane constituents. The polycarbonate-polydiorganosiloxane terpolymers may be represented by the general formula

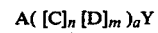

wherein A is a member selected from the group consisting of hydrogen and a phenyl radical; Y is a member selected from the group consisting of OH and a phenoxy radical; n is equal to from 1 to about 20, and preferably from 1 to about 10; m is equal to from 1 to about 10, and preferably from 1 to about 5; a is equal to from 1 to about 30, and preferably from 1 to about 10; C is a halocarbonate-carbonate copolymer containing the following two units in random fashion in the linear chain

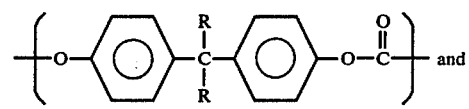

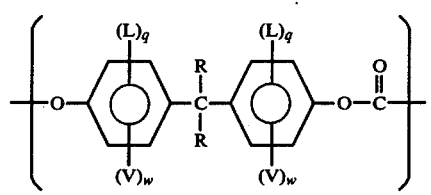

wherein R is independently selected from hydrogen and hydrocarbon radicals, preferably lower alkyl radicals; V is independently selected from halogen radicals, preferably bromine radicals; L is independently selected from lower alkyl radicals, preferably methyl radicals; W has a value of from 1 to 4; q has a value of from 0 to 2, provided that the sum of q plus w does not exceed 4; D is a carbonate or halocarbonate chain-stopped polydiorganosiloxane selected from the group represented by the general formulas

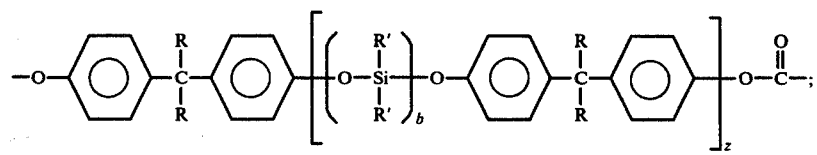

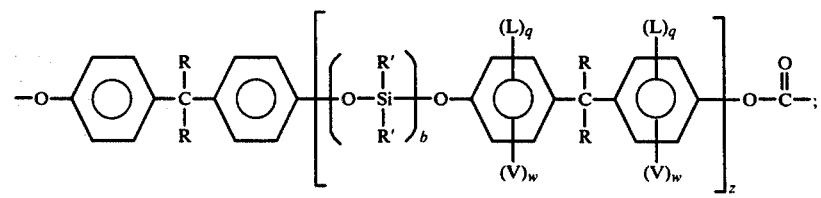

and

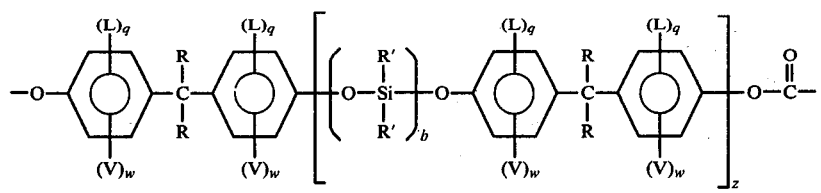

VI.

wherein L, V, q, w, and R are as defined above; z has a value of from 1 to about 4; b is equal from 2 to about 20, preferably from 5 to about 15; and R' is independently selected from the class of hydrocarbon radicals, preferably lower alkyl radicals, and halogenated hydrocarbon radicals, preferably halogenated lower alkyl radicals, and more preferably from lower alkyl radicals.

The terpolymers of formula I can be produced by first reacting under substantially anhydrous conditions at temperatures in the range of 0° C. to 100° C. and in the presence of an acid acceptor, such as ammonia, a halogenated chain-stopped polydiorganosiloxane having the formula

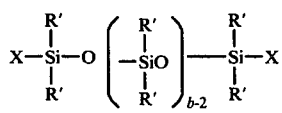

VII.

wherein X is a halogen radical, preferably chloro, and a dihydric phenol having the formula

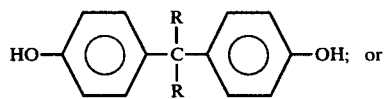

VIII.

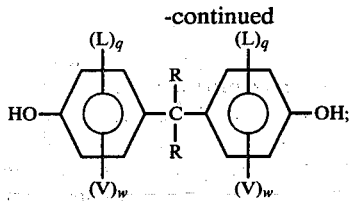

IX.

or a mixture of dihydric phenols of formulas VIII and IX to form a compound represented by the formula

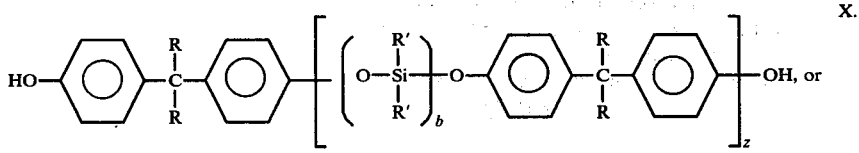

X.

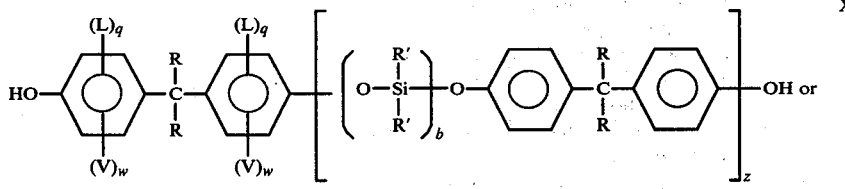

XI.

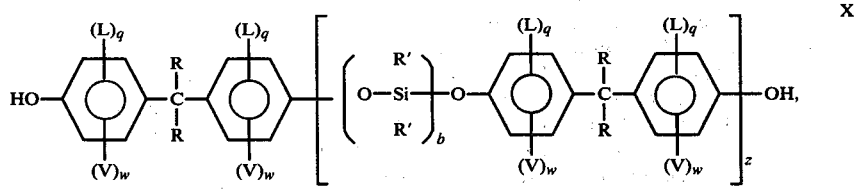

XII.

wherein L, V, R, R', b, q, z and w are as defined above. Compounds represented by formula X are formed by reacting a diorganopolysiloxane of formula VII with a dihydric phenol of formula VIII, compounds of formula XI are formed by reacting a diorganopolysiloxane represented by formula VII with a dihydric phenol represented by formula VIII and a dihydric phenol represented by formula IX, and compounds represented by formula XII are formed by reacting a diorganosiloxane of formula VII with a dihydric phenol represented by formula IX. The compounds of formula X, XI or XII are then admixed with a mixture of dihydric phenols represented by the formulas VIII and IX, and the resulting admixture is phosgenated, i.e., treated with a precursor of carbonic acid such as carbonyl chloride until the resulting mass achieves maximum viscosity.

Thus, the terpolymers of formula I are the intercondensation products of (i) a dihydric phenol; (ii) a halogenated, preferably brominated, dihydric phenol; (iii) a dihydric phenol and/or halogenated dihydric phenol chain-stopped polydiorganosiloxane, wherein said polydiorganosiloxane is composed of chemically combined diorganosiloxy units consisting essentially of dialkylsiloxy units which are connected to each other by silicon-oxygen-silicon linkages wherein each of the silicon atoms has two organo radicals, preferably lower alkyl radicals, attached through a carbon-silicon bond and where said dihydric phenol and the polydiorganosiloxane are joined by aryloxy-silicons linkages; and (iv) a carbonyl halide, preferably carbonyl chloride.

The halogenated chain-stopped polydiorganosiloxanes of Formula VII can be made by conventional procedures such as by the controlled partial hydrolysis of a diorganodihalosilane, for example, dimethyldichlorosilane as taught in Patnode U.S. Pat. No. 2,381,366 and Hyde U.S. Pat. Nos. 2,629,726 and 2,902,507. Another procedure that can be employed involves equilibrating a mixture of a diorganodichlorosilane and a cyclic polydiorganosiloxane in the presence of a metal catalyst such as ferric chloride as shown in Sauer U.S. Pat. No. 2,421,653. Although the various procedures utilized in forming the halogenated polysiloxane are not critical, generally it has been found desirable to maintain the halogen content of the resulting halogenated polysiloxane in the range of about 1 to about 35 percent, by weight, and preferably from about 2 to about 15 percent by weight of said halogenated polysiloxane. The halogenated polysiloxane is preferably in the form of a chlorinated polydimethylsiloxane.

Dihydric phenols that are included in Formulas VIII and IX are for example, 2,2-bis(4-hydroxyphenyl)propane (bisphenol-A); 2,4'-dihydroxydiphenylmethane; bis-(2-hydroxyphenyl)-methane; bis(4-hydroxyphenyl)-methane; 1,1-bis-(4-hydroxyphenyl)-ethane; 1,1-bis(4-hydroxy-2-chlorophenyl)-ethane; 1,1-bis-(2,5-dimethyl-4-hydroxyphenyl)-ethane; 2,2-bis(3-isopropyl-4-hydroxyphenyl)-propane; 2,2-bis(4-hydroxy-3,5-dibromophenyl)-propane; 2,2-bis(4-hydroxy-2-bromophenyl)-propane; 2,2-bis(4-hydroxy-3,5-dibromo-2,6-dimethylphenyl)-propane, etc.

In the practice of the invention, an anhydrous mixture of the halogenated polysiloxane of Formula VII, and the polyhydric phenol of Formula VIII, Formula IX, or mixtures thereof, is formed in the presence of a base, and at temperatures sufficient to effect reaction. In the course of the reactions, reaction product, represented by Formulas X, XI, XII or mixtures thereof, is produced in the form of a polydiorganosiloxane that is chain-stopped by a substituted aryloxy-silicon linkage with dihydric phenol radicals. To this reaction intermediate is added a mixture of dihydric phenols represented by Formulas VIII and IX and the resulting mixture is then phosgenated, i.e., treated with a precursor of carbonic acid such as carbonyl chloride or carbonyl fluoride until the resulting mixture attains a maximum viscosity.

The halogenated carbonate component provides radiographically opaque properties for the instant composition, the diorganopolysiloxane component provides the requisite plasticity or flexibility required of a catheter for medical use, and the carbonate component provides the composition with the requisite extrudable properties necessary for forming the tubing.

The amount of diorganopolysiloxane component present in the instant terpolymers can vary within wide limits but is an amount effective to impart the requisite flexibility required of catheters for medical uses. Generally, this amount comprises, in percent by weight, from about 25% to about 70%, preferably from about 35% to about 60% of the terpolymer.

The amounts of carbonate and halogenated carbonate components, preferably brominated carbonate, present in the instant terpolymers can likewise vary within wide limits depending on the degree of radiographic opacity required. In general, the halogenated carbonate can be employed in the terpolymer composition in amounts of from about 5 to about 80 weight percent, preferably from about 10 to 70 weight percent. To have the requisite extrudable properties, the terpolymer generally contains from about 20 to about 95%, by weight of the carbonate component, preferably from about 30 to about 90% by weight.

DESCRIPTION OF THE PREFERRED EMBODIMENTS

The following example is set forth to illustrate more clearly the principle and practice of this invention to those skilled in the art.

EXAMPLE 1

A terpolymer of polycarbonate-polydiorganosiloxane is prepared by placing a mixture of 444.8 grams of a bisphenol-A encapped silicone oligomer solution containing about 15 weight percent of the oligomer and 85 weight percent of methylene chloride solvent, 14 grams of bisphenol-A, 31 grams of tetrabromobisphenol-A, 1.4 grams of triethylamine, 350 ml $H_2O$, and 215 ml of $CH_2Cl_2$ in a vessel. The resulting mixture is then stirred and phosgene is slowly passed into the mixture. NaOH is added to the mixture to keep the pH at about 9–11. Phosgenation of the mixture is continued until the mass achieves maximum viscosity. The phosgenated reaction mixture is then washed with dilute hydrochloric acid and water. The final product is precipitated by adding methanol to the washed reaction mixture.

The terpolymer as prepared in accordance with Example 1 is extruded from a standard extrusion machine. The extruded tubing is clear and transparent to visible light, but is opaque to x-rays.

EXAMPLE 2

Implantation Test—Albino Rabbits

Two healthy, adult New Zealand albino rabbits weighing in excess of 2.5 Kilograms are used as test animals. The rabbits are housed individually and allowed food and water ad libitum.

Approximately 18–24 hours to implantation, the back of each animal is clipped on both sides of the spinal column. All loose hair is removed after clipping and prior to implantation to prevent any possibility of entry into implantation site.

Four strips of steam sterilized terpolymer prepared substantially in accordance with Example 1, approximately 1 mm. wide and 10 mm. long, are introduced into the right paravertebral muscle of each rabbit. Two strips of U.S.P. Negative Control plastic are implanted in the left paravertebral muscle of each rabbit. The implants are made one inch apart lateral and parallel to the spinal column. A 15 gauge trochar needle is used, with the implant positioned even with the pointed end of the needle. The needle is inserted into the muscle at an angle of 30°, then withdrawn over the stylet for a distance sufficient to hold the implant in the tissue. The needle and stylet are withdrawn simultaneously.

The animals are sacrificed, by anesthetic overdose, 72 hours after implantation and the entire paravertebral muscle on each side of the spinal cord is removed. Cross sections of the muscles are made to locate the implants. The tissue surrounding the center portion of each implant is examined grossly for hemorrhage, film and encapsulation.

The requirements of the test are met if the tissue reaction to the test strips in each animal is not significantly greater than at the U.S.P. Negative Control sites.

The results of this test are as follows:

No gross reaction for 72 hours.

Rabbit #1. Autopsy. Macroscopic.

Test Samples: No evidence of tissue reaction.

U.S.P. Negative Controls: No evidence of tissue reaction.

Rabbit #2. Autopsy. Macroscopic.

Test Samples: No evidence of tissue reaction.

U.S.P. Negative Controls: No evidence of tissue reaction.

This example demonstrates the generally physiologically non-toxic nature of the present terpolymer. This non-toxic character of the instant terpolymer allows a catheter formed of this material to be used in biological systems without any adverse effects upon said system.

Although the above examples ahve shown one embodiment of the present invention, variations thereof are possible in light of the above teachings. It is, therefore, to be understood that changes may be made in the particular embodiments of the invention described which are within the full intended scope of the invention as defined by the appended claims.

What is claimed is:

1. A hollow flexible tube which is biologically inert optically non-opaque and radiographically opaque fabricated from a terpolymer represented by the general formula $$A\,([C]_n\,[D]_m)_a\,Y$$

wherein A is selected from the group consisting of hydrogen and a phenyl radical; Y is selected from the group consisting of OH and a phenoxy radical; n has a value of from 1 to about 20; m has a value of from 1 to about 10; a has a value from 1 to about 30; C is a carbonate polymer containing the following two units, in random fashion,

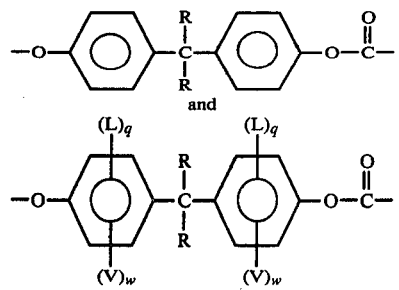

wherein R is independently selected from monovalent hydrocarbon radicals, V is independently selected from halogen radicals, L is independently selected from lower alkyl radicals, W has a value of from 1 to 4, and q has a value of from 0 to 2, provided that the sum of q and w does not exceed 4, and D is a carbonate end-capped polydiorganosiloxane.

2. The tube of claim 1 wherein V is bromine and w has a value of 2.

3. The tube of claim 2 wherein said carbonate chain stopped polydiorganosiloxane is represented by the general formula

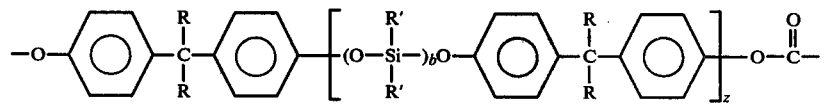

wherein R and R' are independently selected from hydrocarbon radicals, b has a value of from 2 to about 20, and z has a value of from 1 to about 4.

4. The tube of claim 2 wherein said carbonate chain stopped polydiorganosiloxane is represented by the general formula

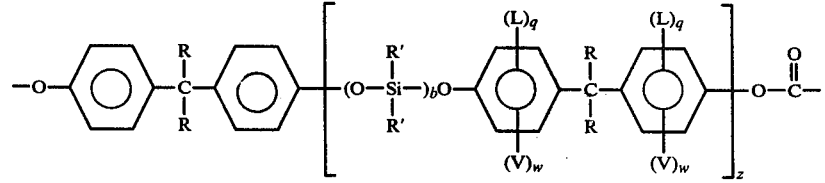

wherein R and R' are independently selected from hydrocarbon radicals; L is independently selected from lower alkyl radicals; V is independently selected from halogen radicals; q has a value of from 0 to 2 and w has a value of from 1 to 4, provided that the sum of w and q does not exceed 4; z has a value of from 1 to about 4; and b has a value of from 2 to about 20.

5. The tube of claim 2 wherein said carbonate chain stopped polydiorganosiloxane is represented by the general formula

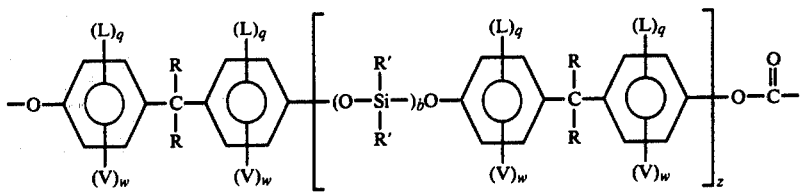

wherein R and R' are independently selected from hydrocarbon radicals; L is independently selected from lower alkyl radicals; V is independently selected from halogen radicals; q has a value of from 0 to 2 and w has a value of from 1 to 4, provided that the sum of w and q does not exceed 4; z has a value of from 1 to about 4; and b has a value of from 2 to about 20.

6. The tube of claim 4 wherein V is bromine, w is 2 and q is 0.

7. The tube of claim 4 wherein V is bromine, w is 2, L is a methyl radical, and q is 2.

8. The tube of claim 5 wherein V is bromine, w is 2 and q is 0.

9. The tube of claim 5 wherein V is bromine, w is 2, L is a methyl radical, and q is 2.

10. The tube of claim 2 wherein said tube is a catheter.

11. A hollow flexible tube which is biologically inert, optically non-opaque and radiographically opaque comprised of a terpolymer which is the intercondensation product of: (A) (i) a dihydric phenol chain stopped polydiorganosiloxane, (ii) a halogen substituted dihydric phenol chain stopped polydiorganosiloxane, or (iii) a dihydric phenol and halogen substituted dihydric phenol chain stopped polydiorganosiloxane, wherein said polydiorganosiloxane and said dihydric phenol or halogen substituted dihydric phenol are joined by aryloxy-silicon linkages and wherein said polydiorganosiloxane consists essentially of dialkylsiloxy units which are connected to each other by silicon-oxygen-silicon linkages wherein each of the silicon atoms has two organo radicals attached through a carbon-silicon bond; (B) a dihydric phenol; (C) a halogen substituted dihydric phenol; and (D) a carbonyl halide.

12. A hollow tube of claim 11 wherein said dihydric phenol is a bis-phenol and wherein said halogen substituted dihydric phenol is a halogen substituted bisphenol.

13. A hollow tube of claim 12 wherein said halogen substituted bisphenol is a bromo substituted bisphenol.

14. A hollow tube of claim 13 wherein said bromo substituted bisphenol is tetrabromo bisphenol.

15. A hollow tube of claim 11 wherein said bisphenol is 2,2-bis(4-hydroxyphenyl)propane and wherein said halogen substituted bisphenol is 2,2-bis(3,5-dibromo-4-hydroxyphenyl)propane.

* * * * *